United States Patent [19]
Leistritz

[11] Patent Number: 5,226,921
[45] Date of Patent: Jul. 13, 1993

[54] CONTROL OF THE AIR RATIO IN A HOT EXHAUST GAS STREAM AND OXYGEN PROBE THEREFOR

[75] Inventor: Klaus Leistritz, Zurzach, Switzerland

[73] Assignee: Klaus Leistritz Engineering AG, Zurich, Switzerland

[21] Appl. No.: 793,361
[22] PCT Filed: Apr. 22, 1991
[86] PCT No.: PCT/CH91/00092
§ 371 Date: Dec. 20, 1991
§ 102(e) Date: Dec. 20, 1991
[87] PCT Pub. No.: WO91/17434
PCT Pub. Date: Nov. 14, 1991

[30] Foreign Application Priority Data
Apr. 27, 1990 [CH] Switzerland ............... 1444/90

[51] Int. Cl.⁵ .................................... F02M 7/00
[52] U.S. Cl. .................................... 123/703
[58] Field of Search ............ 123/703, 704, 672, 435, 123/697

[56] References Cited
U.S. PATENT DOCUMENTS

| | | | |
|---|---|---|---|
| 4,377,143 | 3/1983 | Hamburg | 123/672 |
| 4,592,315 | 6/1986 | Kobayashi et al. | 123/672 |
| 4,601,276 | 7/1986 | Damson et al. | 123/672 |
| 4,765,298 | 8/1988 | Kojima et al. | 123/697 |
| 4,834,051 | 5/1989 | Tanaka et al. | 123/703 |
| 4,889,098 | 12/1989 | Suzuki et al. | 123/697 |
| 4,944,273 | 7/1990 | Baresel et al. | 123/703 |
| 4,957,705 | 9/1990 | Uchikawa | 123/703 |

FOREIGN PATENT DOCUMENTS

3743295 7/1988 Fed. Rep. of Germany ...... 123/703

*Primary Examiner*—Raymond A. Nelli
*Attorney, Agent, or Firm*—Bachman & LaPointe

[57] ABSTRACT

A method for controlling the fuel-air mixture in an Otto engine having at least one cylinder, especially in an automobile engine, for the optimum use of a catalyser (18) with a probe in the hot exhaust gas stream (20) containing carbon monoxide, nitrogen oxides and hydrocarbons. The measuring signals of the probe are converted through electronic means into control signals for the mixture preparation and ignition. The oxygen content of the exhaust gas stream gas stream (20) is measured in the combustion chamber of the cylinders, beyond the outlet valve in the cylinder heads or in the single pipes (12), in the protective region of a smooth, aerodynamic deflection device (40) without a reference atmosphere with a resistive ceramic oxygen probe (24) having a heat resistance up to approximately 1300° C. and an adjustment time within the millisecond range.

17 Claims, 3 Drawing Sheets

CONTROL OF THE AIR RATIO IN A HOT EXHAUST GAS STREAM AND OXYGEN PROBE THEREFOR

BACKGROUND OF THE INVENTION

The invention relates to a method for controlling the air-fuel mixture in an Otto engine having at least one cylinder, especially in an automobile engine, for the optimum use of a catalyzer with a probe which serves to determine the air ratio in a hot exhaust gas stream with carbon monoxide, nitrogen oxides and hydrocarbons, in which the measuring signals of the probe are converted with an electronic means into control signals for the ignition and mixture preparation. The invention further relates to a device for carrying out the method.

An Otto engine, an engine with a spark ignition, e.g. an automobile petrol engine, a stationary petrol engine or a two-stroke petrol engine, produces essentially carbon dioxide, but also carbon monoxide, nitrogen oxide and hydrocarbons, which are discharged into the environment. Whereas the carbon monoxide and the nitrogen oxides relate to chemically defined compounds, the hydrocarbons comprise a large number of compounds.

Automobile engines especially these days are subjected to increasingly strict exhaust gas standards which permit only limited residual quantities of the harmful gases mentioned. In the exhaust gas cleaning technology for Otto engines driven by petrol, a central role is played by catalyzers controlled by a lambda probe, especially three-way catalyzers, but also oxidation and/or twin-bed catalyzers. In a series of chemical reactions, for example in a three-way catalyzer, the harmful exhaust gas components, especially also the heterogenic hydrocarbons, are converted with approximately 90% efficiency into water, carbon dioxide, nitrogen and hydrogen.

The simultaneous reaction of the harmful exhaust gases of carbon monoxide, nitrogen oxides and hydrocarbons assumes that a ratio of the air-fuel mixture around the stoichiometric value $\lambda=1$ is adhered to within strict limits. Lambda is also used to represent the air ratio:

$$\lambda = \frac{\text{air quantity supplied}}{\text{theoretical air requirement}}$$

$\lambda<1$ refers to a rich mixture, $\lambda>1$ refers to a lean mixture.

A lambda probe supplies a voltage signal to an electronic control which in turn signals to a mixture preparation device whether the mixture is to be enriched or made leaner. However, the change in the air-fuel mixture must not take place suddenly, an integrator changes the mixture composition and, if necessary, it changes the ignition timing slowly as a function of time. The air-fuel mixture thus deviates constantly by a few percent around $\lambda=1$, even during optimum operation.

According to the present-day state of the art, lambda probes are arranged before the catalyzer in the exhaust gas flow direction approximately 1 m down-stream behind the exhaust gas quarter bend, in the collecting pipe in the case of multi-cylinder engines.

A lambda probe operates according to the principle of a galvanic oxygen concentration cell with a solid body electrolyte of zirconium dioxide which is stabilised with yttrium oxide. The solid body electrolyte is protected with a metal mesh—also known as metal cage—, which dampens the force of the hot exhaust gas stream. The exhaust gas flows round the outer surface of the solid body electrolyte, while the inner open chamber is connected to the atmosphere as reference gas.

Despite its obvious advantages, the lambda probe also has disadvantages:

It operates only at temperatures from approximately 400° C. upwards. During the critical period prior to the catalyzer being heated, the air-fuel mixture is not regulated, or the lambda probe must be pre-heated.

The maximum continuous operating temperature is approximately 800° C. The probe must be arranged in a cooler area of the collecting pipe, relatively far back in the flow direction.

The lamda probe has a response time of 50 to 100 msec. which, together with the long delay of the exhaust gas prior to reaching the probe, amounts to a very long reaction time for engines operating at high speeds.

The lambda probe provided with a metal mesh or metal cage has a large effective cross-section and therefore substantially interferes with the exhaust gas stream.

The CH-A5 666 724 describes a lambda probe which has a solid body electrolyte withdrawn from the exhaust gas stream. Whilst the lambda probe seated on a tubular holder is less likely to be overheated and does not interfere with the exhaust gas stream, being situated further back, however, it is even more sluggish with regard to the reaction time, the exhaust gas stream flowing unhindered no longer flows directly round the solid body electrolyte, but only after a branched-off partial stream has passed through a relatively small opening.

The DE-C1 3 743 295 sets out to prevent the probe ceramics from being destroyed by liquid droplets falling onto a heated lambda probe during cold starting. Also, the representation of the signals delivered by the lambda probe is intended to be improved. For this purpose a gas deflection plate is arranged upstream of the lambda probe in such a way that the lambda probe is situated in the flow shadow. The lambda probe protected by a relatively large cage of known construction is arranged in the collecting pipe of the exhaust system and captures part of the entire exhaust gas stream of all the cylinders in a region with an already relatively low gas temperature.

It is the object of the present invention to provide a method of the type mentioned at the beginning and a device for carrying out the method which permit a more selective engine control with probes and associated control electronics which respond substantially more quickly than was hitherto the case.

SUMMARY OF THE INVENTION

With reference to the method, the object according to the invention is achieved in that the oxygen content of the exhaust gas stream is measured in the combustion chamber of the cylinders, after the outlet valve in the cylinder heads, or in the single pipes, by measuring without a reference atmosphere in the protective area of a smooth, aerodynamic deflection device with a resistive ceramic oxygen probe having a heat resistance of up to approximately 1300° C. and an adjustment time within the millisecond range. Special and further developing embodiments are the subject of the dependent patent claims.

The deflection device arranged in the selective cylinder exhaust gas stream simultaneously carries out several functions:

It forms a heat shield for the oxygen probe, which protects against the direct effect of the discharging exhaust gases of very high temperature produced in an explosion-like manner. However, the deflection device which is at least partly open in relation to the exhaust gases downstream in the flow direction ensures that directly and unmixed a part of the exhaust gas stream always flows around the probe. With the oxygen probe arranged in a completely closed or substantially closed deflection device, the advantage of a quick response time would be at least partly cancelled out, similar to an arrangement of a probe according to CH-A5 666724.

The metal deflection device removes heat from the protective region for the oxygen probe situated in the exhaust gas stream and conducts this to the outside. This improves the heat protection still further.

Because of the small dimensions of the probe, the exhaust gas stream is only insignificantly affected even in single pipes by the small construction of the smooth, aerodynamic deflection device and therefore does not affect engine efficiency or only insignificantly.

A conventional lambda probe with the necessary protective cage for purely geometric reasons alone could not be arranged in a single pipe and despite deflection plate would never be able to withstand the high temperatures of the method according to the invention.

According to the invention, the oxygen content is measured with an adjustment time of 1 to 20 msec, preferably 3 to 15 msec. With a response time of a few milliseconds, the resistive oxygen probe can measure and adjust the air-fuel mixture of each individual piston stroke even in engines running at high speeds, for example 6000 revolutions per minute. For dynamic drive situations, especially when accelerating, with a downstream catalyzer the fuel consumption and thus the emission of harmful exhaust gases can be reduced to a minimum. In the first place this is of great significance during the cold starting phase, during which a short response time is essential.

The high degree of heat resistance of the oxygen sensor operating without a reference atmosphere, in cooperation with the smooth, aerodynamic deflection device, allows the oxygen content to be measured in the combustion chamber of the cylinders, after the outlet valve in the cylinder heads or in the single pipes of the exhaust system. Of particular practical interest is the measurement of the oxygen ratio directly after the inlet opening of a single pipe of the exhaust system. Only these measuring points, situated outside the operating area of the conventional lambda probes, allow a selected cylinder to be controlled, i.e. the optimum combustion in each cylinder.

For the sake of completeness, it is emphasized once more that with the classical lambda probes the oxygen content of the exhaust gas stream can only be measured in the collecting pipe of the exhaust system.

Because of the deflection device, the oxygen probe as a rule has an adequate heat resistance up to approximately 1300° C. even in very hot parts of the engine. In the said preferred region for measuring the oxygen content, the inlet region to the single pipes, the temperature as a rule is around 900° to 1100° C.

Although resistive ceramic oxygen probes start to react at a temperature of 20° C., an arrangement in hot to very hot exhaust gases is advantageous, because the delay time is shortest after ignition of the gases until the exhaust gases reach the oxygen probe and, for adjusting the oxygen content, the optimum permanent temperature of the oxygen probe for regulating the air-fuel mixture is quickly reached.

The further simplification of the measuring method is helped by the fact that a resistive oxygen probe operating without a reference atmosphere, apart from high temperatures, is also resistant to high pressures without affecting the quick response time within the millisecond range.

With reference to the device, the object is achieved according to the invention in that an oxygen probe with specific electrical conductivity dependent on the oxygen partial pressure, as the thin diffusion layer of a semiconducting titanate on a small ceramic support, is arranged on the leeward or downstream side of an aerodynamic deflection surface which is at least partly open downstream in the combustion chamber of the cylinder, after the outlet valve in the cylinder heads or in the single pipes. Special and further developing embodiments are the subject of the dependent patent claims.

The active layer of the oxygen sensor preferably has a two-dimensional expansion of from 0.5 to 10 mm$^2$ and a thickness of 1 to 20 $\mu$m, especially 5 to 10 $\mu$m. The application preferably takes place by thin or thick-film technology.

An oxygen sensor of small dimensions, which is known per se and which is freely available, is of considerable significance for a number of reasons:

The sensor adjustment time is dependent on the layer thickness; the thinner the layer, the shorter the adjustment time.

The flow behaviour of the exhaust gases should be disturbed as little as possible by the oxygen probe. This can best be achieved by a deflection surface in which the sensor to be protected is as small as possible. The closer the oxygen probe is arranged to a combustion chamber, the more important become flow optimization and thus, according to the invention, an effective combination of deflection surface and oxygen probe for producing a homogenous flow around the same.

Smaller oxygen probes and thus smaller deflection surfaces result in smaller manufacturing and assembly costs.

The diffusion layer which absorbs oxygen in proportion to the partial pressure preferably consists of calcium, strontium or barium titanate with doping material known per se. The conductivity as a function of the oxygen partial pressure is the result of a change in the concentration of atomic defects. Because of its direct dependence on the oxygen partial pressure, this electric conductivity requires no reference atmosphere.

Newly fitted or exchanged oxygen probes preferably have an oxygen-absorbing diffusion layer which already contains the impurities present in the exhaust gas stream. A balance therefore always exists right from the start, which therefore immediately allows an optimum adjustment of the oxygen content even during a refit.

The oxygen probe and the deflection surface are preferably constructed as one module to be rigidly fitted or which can preferably be exchanged.

The deflection surface is made from a heat-resistant and corrosion-proof material which is also abrasion-resistant, preferably from a metal and/or ceramic material which is smooth and aerodynamically shaped in order to reduce the flow resistance. A deflection plate, e.g. forming the deflection surface, made from metal, preferably a heat-conducting steel or a copper alloy is preferably connected in a heat-conducting manner to a cylinder, a cylinder head or a single pipe of the exhaust gas system.

The leeward side can be varied by changing the embodiment of the deflection surface in various ways. This may be linked to the wall and in this way form the smooth aerodynamic deflection device. According to other variations the wall is not part of the deflection device, but moreover is preferably constructed as a ridge roof, pointed hat, semi- to three quarter sphere or the like.

Briefly summarised once more, the essential advantages of the invention are found to be that an oxygen probe, protected by a smooth, aerodynamic deflection device, with a high degree of heat resistance and a response time in the millisecond range allows a selective control of the cylinders, measurements can take place without a reference atmosphere, and the efficiency of the method is improved.

The smooth, aerodynamic deflection device, with or without oxygen probe, can be preassembled or fitted later.

BRIEF DESCRIPTION OF THE DRAWINGS

The invention is explained in more detail with the aid of embodiment examples shown in the drawing, which are also the subject of the dependent claims. Schematically shown are:

DETAILED DESCRIPTION

Figure 1:
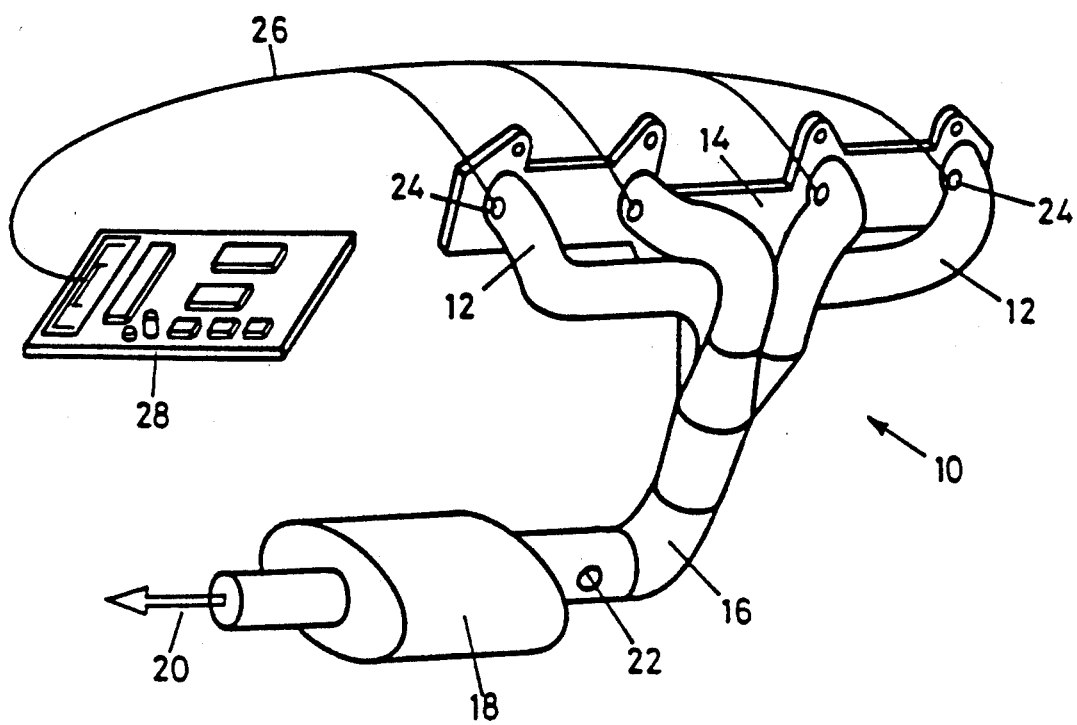
FIG. 1 a perspective view of an exhaust system,
FIG. 2 a perspective view of an oxygen probe,
FIG. 3 a cut open single pipe with a protected probe,
FIG. 4 a cut open side view of FIG. 3,
FIG. 5 a cut open plan view of FIG. 3, and
FIGS. 6–9 variations of smooth, aerodynamic deflection devices with an oxygen probe.

An exhaust system 10 shown in FIG. 1 comprises four single pipes 12 which are fixed to an engine flange 14. The single pipes 12 are combined into an exhaust manifold 16, a collecting pipe.

The exhaust manifold 16 feeds into a three-way catalyzer 18 which reacts with about 90% efficiency with parts of carbon monoxide, nitrogen oxides and hydrocarbons, produced as a result of non-stoichiometric combustion in the hot exhaust gas stream 20, shown by an arrow, to form harmless gases.

A lambda probe 22 of conventional construction would be arranged in the area before the three-way catalyser 18 where the temperature of the exhaust gas stream has dropped to at least approximately 800° C., as a rule to about 600° C.

However, the exhaust system according to FIG. 1 does not contain the usual lambda probe 22 but, as shown in detail in the FIGS. 3 to 9, four resistive ceramic oxygen probes 24 protected by a smooth, aerodynamic deflection device with a high degree of heat resistance and adjustment time for each specific cylinder of approximately 5 msec.

Lambda probes 22 of conventional construction in the area of the single pipes 12, especially adjacent the engine flange 14, would no longer be functional and would be destroyed because of excessively high temperatures if, for geometric reasons, they could be installed at all.

From each of the four oxygen probes 24 an electric conductor 26 leads to the electronics or the electronic control 28, where the measuring signals are converted into control signals for the mixture preparation and ignition (not shown).

Figure 2:
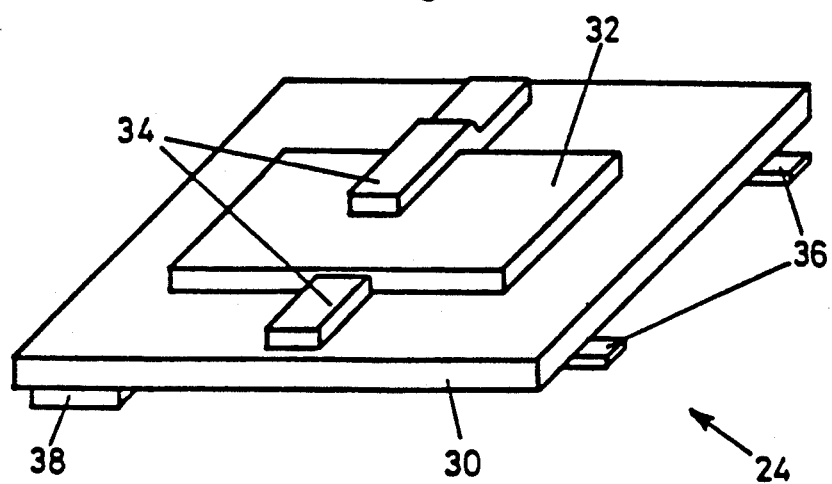

An oxygen probe 24 is shown in detail in FIG. 2. On a ceramic support 30 of dimensions from $5 \times 4 \times 0.8$ mm is applied a thin diffusion layer of strontium titanate, the oxygen sensor 32. This diffusion layer, in the present case manufactured with the aid of thick-film technology, especially a screen printing technique, has a surface of approximately 6 to 8 mm$^2$ and a thickness of approximately 8 to 10 $\mu$m—shown in exaggerated strength. A fine-grained titanate ceramic powder applied to the aluminium oxide substrate, is burnt-on. The electric contact with the diffusion layer 32 is achieved through a thin coating of precious metal, which is also applied by screen printing as before.

For the manufacture of an even thinner diffusion layer 32, is also possible to use the thin-film technology known per se.

The operating current of the oxygen probe 24 is conducted via electric contacts 34 through the diffusion layer which changes its electrical resistance in response to the oxygen partial pressure. The operating current is preferably d.c. In the case of an automobile engine the usual car battery can be used as the current source without any converter units.

Beneath the ceramic support 30 are situated a meandering heating layer 36 and temperature sensor 38, shown only in part. With a heating output of up to 5W, preferably also supplied by the car battery, the diffusion layer 32 can be heated to a temperature of approximately 600° C. through electrical resistance heating. As already mentioned, however, in the present invention this is of less significance because the oxygen probe has a low response temperature and is arranged in an area of high temperature.

Figure 3:
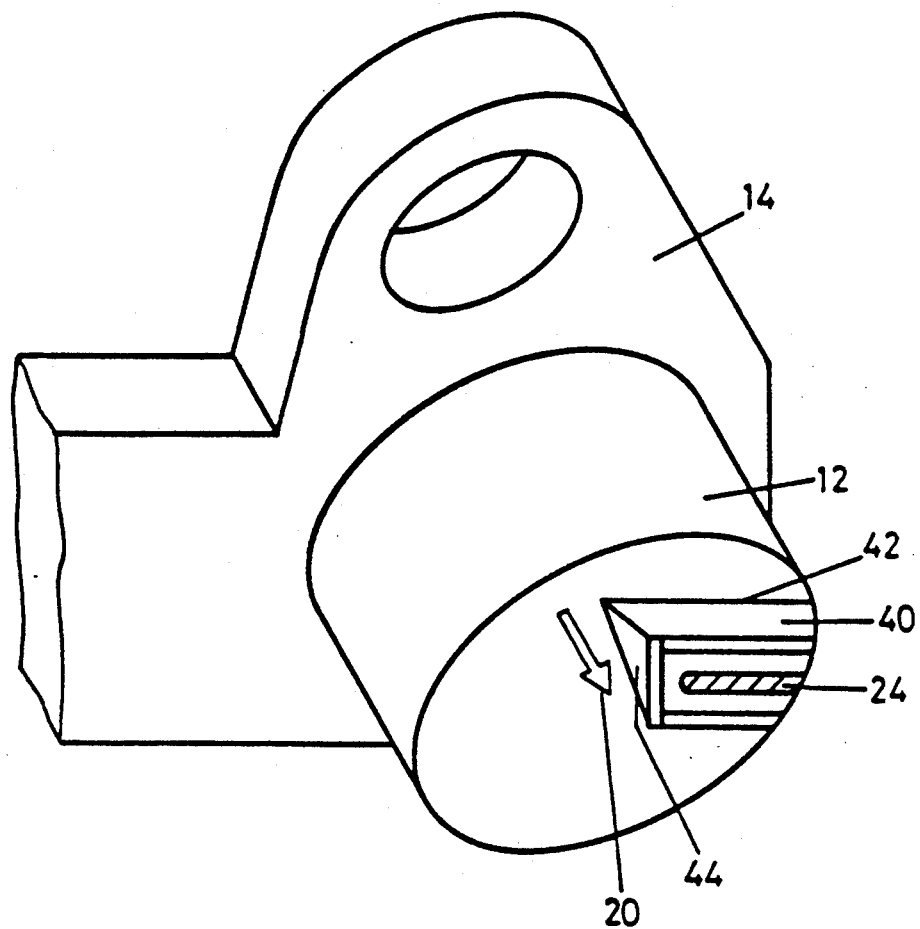

FIG. 3 shows an enlarged cut-out from FIG. 1, but with a cut open single pipe 12. In the proximity of the engine flange 14, where the exhaust gas stream 20 enters the single pipe 12, is arranged a roof-shaped guide plate 40 which protects the oxygen probe 24 from the direct effect of the exhaust gas stream 20 and creates a region sheltered from the gas stream. This allows a homogenous but constantly renewing flow around the oxygen probe 24. The screening effect can be improved still further by the arrangement of a lateral screen 44 extending up to the ridge 42 running perpendicular to the pipe.

Figure 4:
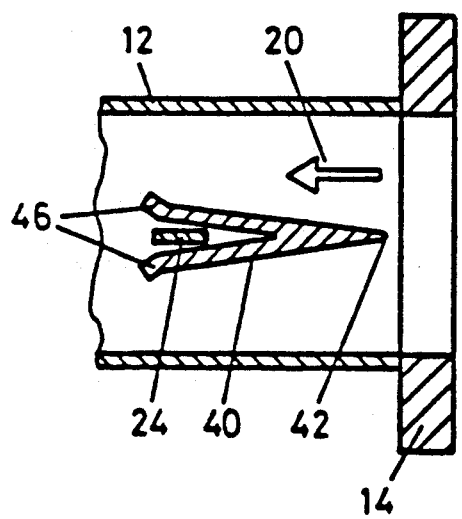
Figure 5:
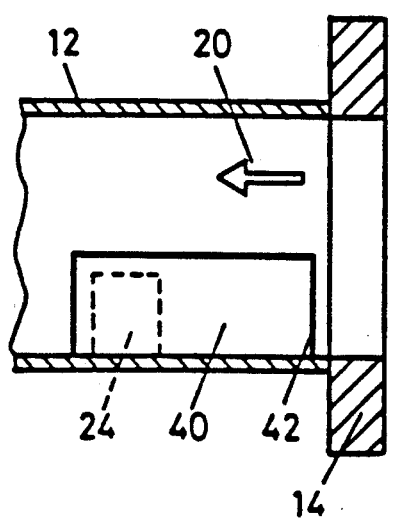

The FIGS. 4 and 5 show even better the protection provided to the oxygen probe 24 by the roof-shaped deflection plate 40. The edges 46 of the deflection plate 40 situated downstream are bent outwards. This does not substantially impede the exhaust gas stream 20, but assists the homogenous flow around the oxygen probe.

Figure 6:
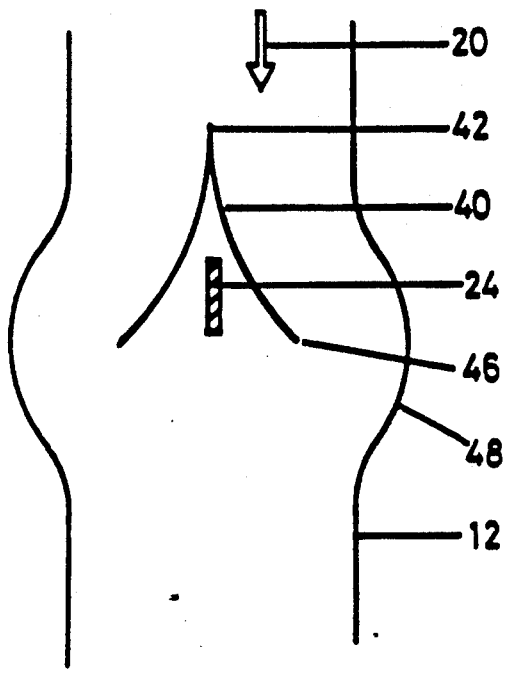
Figure 7:
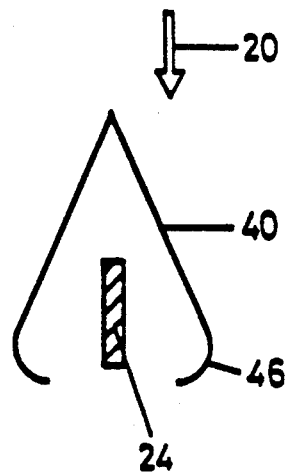

In a single pipe 12 according to FIG. 6 is arranged a roof-shaped deflection plate 40 for an oxygen probe 24, which is shaped to run outwards in a concave manner.

In the region of the lower edges 46 of the deflection plate 40 the single pipe 12 has a bulge 48. This can prevent an exhaust gas build-up, which would reduce engine performance, because of the narrowing of the intermediate space as a result of the deflection plate 40 discharging relatively far on both sides. In the deflection plate 40 according to FIG. 7, also constructed roof-shaped, for creating a region sheltered from the gas stream for an oxygen probe 24, the lower edges 46 are curled inwards.

Figure 8:
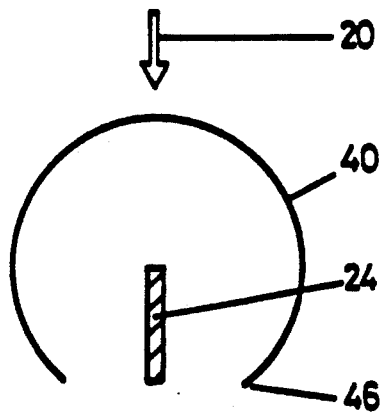

The deflection plate 40 according to FIG. 8 is substantially spherical, with an opening situated downstream.

Figure 9:
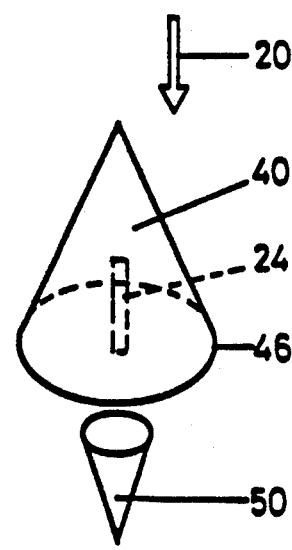

Finally, in FIG. 9 the deflection plate 40 is constructed as a pointed hat or cone. A counter piece 50 to the deflection plate 40 is arranged downstream, also in the shape of a pointed hat. The already slight interference to the flow conditions can thus still be reduced by the arrangement of a deflection plate. Such counter pieces can of course also be used with roof-shaped or differently shaped deflection plates.

I claim:

1. An apparatus for measuring the air ratio in a stream of hot exhaust gas from an Otto engine having at least one cylinder, the apparatus comprising:

an oxygen probe comprising a diffusion layer formed from a semi-conducting titanate on a ceramic support, the probe having an electrical conductivity which is dependent upon oxygen partial pressure, having a resistance to temperatures up to about 1300° C., and operating without a reference atmosphere;

deflecting means for aerodynamically deflecting the stream of hot exhaust gas, disposed in the stream of hot exhaust gas so as to define a protected area downstream of the deflecting means, wherein a flow of hot exhaust gas which is substantially homogeneous and constant circulates through the protected area, and wherein the probe is disposed in the protected area, whereby the probe is shielded from the stream of hot exhaust gas and is exposed to the substantially homogeneous and constant flow of hot exhaust gas;

wherein the Otto engine has a plurality of cylinders each connected through an exhaust pipe to an exhaust manifold where a stream of hot exhaust gas from each cylinder is combined, the oxygen probe and deflecting means being positioned between each cylinder of the plurality of cylinders and the exhaust manifold, whereby the air ratio of the stream of hot exhaust gas from each cylinder is measured; and wherein the deflecting means comprises an aerodynamic deflection surface having an open end facing downstream in the stream of hot exhaust gas, the probe beign disposed in the open end of the deflecting means.

2. An apparatus according to claim 1, wherein the deflection surface comprises a heat resistant and corrosion-proof metal sheet mounted to a wall of an exhaust pipe.

3. An apparatus according to claim 2, wherein the deflection surface is roof-shaped and has a ridge disposed substantially perpendicular to the wall of the exhaust pipe.

4. An apparatus according to claim 3, wherein the roof-shaped deflection surface has concave roof surfaces.

5. An apparatus according to claim 2, wherein the deflection surface is substantially conical in shape.

6. An apparatus according to claim 2, wherein the deflection surface is between semi-spherical to three quarters-spherical in shape.

7. An apparatus according to claim 2, wherein the deflection surface has trailing edges oriented inward, toward the probe.

8. An apparatus according to claim 2, wherein the deflection surface has trailing edges oriented outward, away from the probe.

9. An apparatus according to claim 1, wherein the diffusion layer is formed of a material selected from the group consisting of calcium, strontium and barium titanate, and has an area of between 0.5 to 10 $mm^2$ and a thickness of between 1 to 20 $\mu m$.

10. An apparatus according to claim 9, wherein the diffusion layer has a thickness of between about 5 to about 10 $\mu m$.

11. An apparatus according to claim 1, wherein the diffusion layer contains a concentration by weight of impurities substantially equal to impurities present in the stream of hot exhaust gas.

12. An apparatus according to claim 1, wherein the probe further includes a heating means and a temperature sensor disposed adjacent the ceramic support.

13. An apparatus according to claim 1, wherein the probe and the deflecting means are of modular construction.

14. A method for controlling the air-fuel mixture in an Otto engine having a plurality of cylinders, a stream of hot exhaust gas from each of the plurality of cylinders passing through an exhaust pipe, to an exhaust manifold for combining hot exhaust gas streams from each of the plurality of cylinders, the method comprising the steps of:

providing an oxygen probe comprising a diffusion layer formed from a semi-conducting titanate on a ceramic support whereby the probe has an electrical conductivity which is dependent upon oxygen partial pressure, is resistant to temperatures of up to about 1300° C., and operates without a reference atmosphere;

positioning aerodynamic deflecting means in the streams of hot exhaust gas so as to define a protected area downstream of the deflecting means through which circulates a flow of hot exhaust gas which is substantially homogeneous and constant;

positioning the probe in the protected area, whereby the probe is shielded from the stream of hot exhaust gas and exposed to the substantially homogenous and constant flow of hot exhaust gas;

converting signals from the probe into control signals for ignition and fuel mixture preparation;

positioning the oxygen probe and deflecting means between each cylinder of the plurality of cylinders and the exhaust manifold, whereby the air ratio of the stream of hot exhaust gas from each cylinder is measured; and providing that the deflecting means comprises an aerodynamic deflection surface having an open end facing downstream in the stream of hot exhaust gas, and disposing the probe in the open end of the deflecting means.

15. A method according to claim 14, wherein the positioning step includes positioning the deflecting means and probe sufficiently close to a cylinder of the plurality of cylinders so as to provide an adjustment time of between 1 to 20 msec at a temperature of up to about 1200° C.

16. A method according to claim 14, wherein the positioning step includes positioning the deflecting means and probe sufficiently close to a cylinder of the plurality of cylinders so as to provide an adjustment time of between 3 to 15 msec at a temperature of between 900° to 1100° C.

17. A method according to claim 14, wherein the positioning step includes positioning the deflecting means and probe at an inlet opening of the exhaust pipe.

* * * * *